US009850515B2

(12) United States Patent
McCoy et al.

(10) Patent No.: US 9,850,515 B2
(45) Date of Patent: Dec. 26, 2017

(54) AFFINITY-BASED PARTITION ASSAY FOR DETECTION OF TARGET MOLECULES

(71) Applicant: Bio-Rad Laboratories, Inc., Hercules, CA (US)

(72) Inventors: Adam M. McCoy, Davis, CA (US); Svilen Tzonev, Pleasanton, CA (US); Frank Hsiung, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 997 days.

(21) Appl. No.: 14/173,562

(22) Filed: Feb. 5, 2014

(65) Prior Publication Data

US 2014/0228239 A1    Aug. 14, 2014

Related U.S. Application Data

(60) Provisional application No. 61/762,707, filed on Feb. 8, 2013.

(51) Int. Cl.
*G01N 33/542* (2006.01)
*C12Q 1/00* (2006.01)
*G01N 33/58* (2006.01)

(52) U.S. Cl.
CPC ............ *C12Q 1/00* (2013.01); *G01N 33/542* (2013.01); *G01N 33/581* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. |
| 5,863,736 A | 1/1999 | Haaland |
| 8,831,887 B2 | 9/2014 | Gorfinkel et al. |
| 8,940,882 B2 | 1/2015 | Collis |
| 2009/0117600 A1 | 5/2009 | Brown et al. |
| 2010/0173394 A1 | 7/2010 | Colston, Jr. et al. |
| 2010/0203538 A1 | 8/2010 | Dube et al. |
| 2011/0092373 A1 | 4/2011 | Colston, Jr. et al. |
| 2011/0092376 A1 | 4/2011 | Colston, Jr. et al. |
| 2012/0136147 A1 | 5/2012 | Winger et al. |
| 2012/0164652 A1 | 6/2012 | Clemens et al. |
| 2012/0219961 A1 | 8/2012 | Bruno et al. |
| 2012/0329664 A1 | 12/2012 | Saxonov et al. |
| 2014/0178889 A1 | 6/2014 | Do et al. |

FOREIGN PATENT DOCUMENTS

| | | |
|---|---|---|
| EP | 1615948 A2 | 1/2006 |
| WO | 02/33396 A1 | 4/2002 |
| WO | 2010/036352 A1 | 4/2010 |

(Continued)

OTHER PUBLICATIONS

Extended European Search Report from EP Appln. No. 14748862.1, dated Dec. 6, 2016, 11 pages.

(Continued)

*Primary Examiner* — Jacob Cheu
(74) *Attorney, Agent, or Firm* — Kilpatrick Townsend & Stockton LLP

(57) ABSTRACT

The present invention provides methods of detecting a target molecule in a sample comprising incubating the sample with two or more detectably labeled probes, partitioning the sample into multiple partitions, and detecting the presence of the two or more probes in the same partition.

14 Claims, 7 Drawing Sheets

(56) References Cited

FOREIGN PATENT DOCUMENTS

WO    2012/129187 A1    9/2012
WO    2013/019751 A1    2/2013

OTHER PUBLICATIONS

Partial supplementary European search report from EP Appln. No. 14748862.1, dated Sep. 2, 2016, 8 pages.
International Search Report and Written Opinion dated Apr. 28, 2014 issued for PCT Application No. PCT/US2014/014936, 15 pages.
Gibson, et al., "A novel method for real time quantitative RT-PCR", *Genome Research*, vol. 6, No. 10, pp. 995-1001 (1996).
Heid et al., "Real Time Quantitative PCR", *Genome Research*, vol. 6, pp. 986-994 (1996).
Holland et al., "Detection of specific polymerase chain reaction product by utilizing the 5'-3'exonuclease activity of Thermus aquatics DNA polymerase", *Proc. Natl. Acad. Sci. USA*, vol. 4 , No. 88, pp. 7276-7280 (1991).
Livak et al., "Oligonucleotides with Fluorescent Dyes at Opposite Ends Provide a Quenched Probe System Useful for Detecting PCR Product and Nucleic Acid Hybridization", *PCR Methods and Applications*, vol. 4, pp. 357-362 (1995).
McDermott et al., "Multiplexed target detection using DNA-binding dye chemistry in droplet digital PCR", *Anal. Chem.*, vol. 85, No. 23, pp. 11619-11627 (2013).
Tyagi et al., "Molecular beacons: probes that fluoresce upon hybridization", *Nature Biotechnology*, vol. 14, pp. 303-308 (1996).

AFFINITY-BASED PARTITION ASSAY FOR DETECTION OF TARGET MOLECULES

CROSS-REFERENCE TO RELATED APPLICATIONS

The present application claims priority to U.S. Provisional Application No. 61/762,707, filed Feb. 8, 2013, which is incorporated by reference herein for all purposes.

BACKGROUND OF THE INVENTION

Quantifying the amount of biomolecules in a sample from a subject can provide useful information for a number of clinical applications. One method for detecting and quantifying biomolecules, such as proteins, is by enzyme-linked immunosorbent assay (ELISA). However, the limit of detection and precision of quantification with this assay are not sufficient for many needs. Alternative techniques such as immunoPCR have the potential to increase the sensitivity of detection, but in practice are limited by the problem of high background signal due to non-specific binding of antibody.

Thus, there remains a need for methods of detecting and quantifying biomolecules that offer improved precision of quantification and low end sensitivity.

BRIEF SUMMARY OF THE INVENTION

In one aspect, the present invention provides methods of detecting a target molecule in a sample. In some embodiments, the method comprises:
  incubating a sample in a mixture with at least a first probe linked to a first label and a second probe linked to a second label, wherein the first and second probes specifically bind to the same target molecule, if present;
  partitioning the sample into two or more partitions; and
  detecting the presence of the two or more probes (e.g., the first probe and the second probe) in at least one same partition; thereby detecting the target molecule in the sample.

In another aspect, the present invention provides methods of detecting a target molecule in a sample, wherein the target molecule is linked to, or is capable of generating, a detectable molecule. In some embodiments, the method comprises:
  incubating a sample in a mixture with at least a first probe linked to a first label, wherein the first probe specifically binds the target molecule, if present;
  partitioning the sample into two or more partitions; and
  detecting the presence of the first label and the detectable molecule in at least one same partition; thereby detecting the target molecule in the sample.

In yet another aspect, the present invention provides methods of detecting interaction of at least a first target molecule and a second target molecule that form a complex in a sample. In some embodiments, the method comprises:
  incubating a sample in a mixture with at least a first probe linked to a first label and a second probe linked to a second label, wherein the first probe specifically binds the first target molecule, if present, and the second probe specifically binds the second target molecule, if present;
  partitioning the sample into two or more partitions; and
  detecting the presence of the first label and the second label in at least one same partition; thereby detecting the target molecule in the sample.

In still another aspect, the present invention provides methods of detecting a target molecule or interaction of target molecules in a sample, the method comprising:
  incubating a sample in a mixture with at least a first probe linked to a first label that generates a detectable signal and a second probe linked to a second label, wherein the first probe specifically binds the target molecule, if present in the sample, and wherein the second probe specifically binds the same target molecule as the first probe or to a second target molecule that interacts with the target molecule that the first probe specifically binds to, if present in the sample;
  partitioning the sample into two or more partitions; and
  detecting the quenching of the detectable signal generated by the first label and/or the second label in at least one partition; thereby detecting the target molecule or interaction of target molecules in the sample.

In yet another aspect, the present invention provides methods of detecting a target molecule in a sample, the method comprising:
  incubating a sample in a mixture with at least a first probe linked to a first label and a second probe linked to a second label, wherein the first probe specifically binds to a molecular component that interacts with the target molecule and the second probe competes with the target molecule for interacting with the molecular component;
  partitioning the sample into two or more partitions; and
  detecting a reduction in the number of partitions expressing both the first label and the second label; thereby detecting the target molecule.

In some embodiments, the method is repeated at two or more dilutions and the results are used to correct for background signal. In some embodiments, the method comprises partitioning the sample into at least a first partition library having at least two partitions and a second partition library having at least two partitions, wherein the first and second partition libraries are formed at different dilutions and/or have different volumes per partition. In some embodiments, a single library of partitions is generated where the volume of the partitions vary such that there is at least partitions of two different volumes.

In some embodiments, the partitioning comprises generating a sufficient number of partitions such that at least a majority of partitions have no more than five copies of the target molecule.

In some embodiments, the first and second labels comprise nucleic acids, fluorescent moieties, affinity tags, or click chemistry moieties, and the first label is different from the second label. In some embodiments, the first label generates a first signal and the second label generates a second signal and the first signal and the second signal are distinguishable.

In some embodiments, at least one label is an enzyme. In some embodiments, the first label is a first enzyme and the second label is a second enzyme, and the detecting comprises detecting products generated by the first and second enzymes. In some embodiments, the first and second enzymes are selected from the group consisting of horseradish peroxidase, β-galactosidase, luciferase, alkaline phosphatase, and an esterase that hydrolyzes fluorescein diacetate. In some embodiments, following the partitioning the partitions are incubated, thereby amplifying signal generated by the first and second enzymes. In some embodiments, the activity of the first and second enzymes is inhibited prior to the partitioning.

In some embodiments, the first label and the second label combine to produce a signal that is not generated in the absence of the first label, the second label, or both. In some embodiments, the first label is a first enzyme and the second label is a second enzyme and the activities of the first and second enzymes combine to generate a detectable signal indicative of the presence of the first and second labels.

In some embodiments, the second label quenches the signal generated by the first label. In some embodiments, the first and second labels are members of a fluorescent resonance energy transfer (FRET) pair.

In some embodiments, the signal from the first label and the signal from the second label are amplified following the partitioning. In some embodiments, the first and second labels are nucleic acid labels. In some embodiments, the nucleic acid labels are amplified to generate an amplicon and the detecting comprises detecting the amplicon. In some embodiments, the detecting comprises detecting a fluorescent signal associated with the amplicon. In some embodiments, the fluorescent signal is generated from a fluorescently-labeled polynucleotide probe. In some embodiments, the fluorescent signal is generated from one or more primers used to amplify the nucleic acid labels. In some embodiments, the fluorescent signal is generated from a fluorescent intercalating dye.

In some embodiments, the method further comprises determining the number of partitions comprising the first label and the second label.

In some embodiments, the partitions are droplets or microchannels. In some embodiments, the droplets are surrounded by an immiscible carrier fluid.

In some embodiments, the first probe and/or the second probe comprises a binding agent independently selected from the group consisting of antibodies, aptamers, and non-antibody protein scaffolds. In some embodiments, the first probe and/or the second probe comprises a target-specific binding agent independently selected from the group consisting of a nucleic acid and a zinc finger protein. In some embodiments, the first probe is linked to the target molecule prior to the incubating. In some embodiments, the method comprises incubating the sample in a mixture with more than two probes (e.g., 3, 4, 5, 6, 7, 8, 9, 10 or more probes).

In some embodiments, the target molecule is a protein. In some embodiments, the target molecule is a nucleic acid. In some embodiments, the target molecule is DNA. In some embodiments, the target molecule is RNA. In some embodiments, the target molecule is miRNA or mRNA. In some embodiments, the target molecule is not amplified or ligated before the detecting. In some embodiments, the target molecule is not amplified or ligated before the partitioning.

In some embodiments, the target molecule is an enzyme capable of converting a substrate in the mixture into a detectable molecule or into an intermediate molecule that is further converted into the detectable molecule by the first label. In some embodiments, the target molecule is linked to or bound by the detectable molecule. In some embodiments, the target molecule comprises a fluorescent moiety.

In some embodiments, wherein two or more target molecules that interact or form a complex are to be detected, the first and second target molecules are proteins.

In some embodiments, the molecular component is an enzyme and the target molecule is a substrate for the enzyme.

In some embodiments, wherein a reduction in the number of partitions expressing a first label and/or a second label or a reduction in signal from the first label and/or second label is measured, the measurement is relative to a control sample from which the target molecule is known to be absent.

In some embodiments, the method comprises analyzing the sample using two or more concentrations of at least one component of the mixture to distinguish target molecule-specific co-localization from random co-localization. In some embodiments, the method comprises estimating the amount and/or concentration of the target molecule in the sample by subtracting the expected number of random co-localization events for the sample from the observed number of co-localization events for the sample.

In still another aspect, the present invention provides partition libraries comprising two or more partitions. In some embodiments, at least some partitions comprise a first probe comprising a first label and a second probe comprising a second label. In some embodiments, the partition library comprises at least 500 partitions.

In some embodiments, a majority of the partitions comprise a first probe comprising a first label and a second probe comprising a second label. In some embodiments, the first probe and/or the second probe comprises a binding agent selected from the group consisting of antibodies, aptamers, and non-antibody protein scaffolds. In some embodiments, the first and second labels are nucleic acids, fluorescent moieties, affinity tags, or click chemistry moieties, and wherein the first label is different from the second label. In some embodiments, the first label generates a first signal and the second label generates a second signal and the first signal and the second signal are distinguishable. In some embodiments, the first label is a first enzyme and the second label is a second enzyme and the activities of the first and second enzymes combine to generate a detectable signal indicative of the presence of the first and second labels.

In some embodiments, at least some partitions comprise one or more target molecules. In some embodiments, on average no more than 5 copies of the one or more target molecules are present in each partition.

In some embodiments, the partitions are droplets. In some embodiments, the droplets are surrounded by an immiscible carrier fluid. In some embodiments, the partitions are microchannels. In some embodiments, the partitions are microcapsules.

Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier ($4^{th}$ ed. 2007); Sambrook et al., MOLECULAR CLONING, A LABORATORY MANUAL, Cold Spring Harbor Lab Press (Cold Spring Harbor, N.Y. 1989). The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

As used herein, the term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

The term "probe" refers to a molecule (e.g., a protein, nucleic acid, aptamer, etc.) that specifically interacts with or specifically binds to a target molecule. Non-limiting examples of molecules that specifically interact with or specifically bind to a target molecule include nucleic acids (e.g., oligonucleotides), proteins (e.g., antibodies, transcription factors, zinc finger proteins, non-antibody protein scaffolds, etc.), and aptamers.

A "target molecule" refers to a molecule to be detected in a sample. In some embodiments, the target molecule is a peptide, protein (e.g., an antibody, enzyme, growth regulator, clotting factor, or phosphoprotein), polynucleotide (e.g., DNA, such as dsDNA or ssDNA; RNA, such as mRNA or miRNA; or a DNA-RNA hybrid), aptamer, peptide nucleic acid, carbohydrate, virus, virus-like particle, drug compound, metabolite, or cell. In some embodiments, two or more target molecules to be detected in a sample comprise a complex of interacting target molecules (e.g., a ligand-receptor complex of proteins).

The term "binds," with respect to a probe binding to a target molecule, typically indicates that the probe (e.g., an oligonucleotide or an antibody) binds a majority of the target molecule in a pure population, assuming an appropriate molar ratio of probe to target molecule. For example, a probe that binds a given target molecule typically binds to at least ⅔ of the targets molecules in a solution (e.g., 75%, 80%, 85%, 90%, 91%, 92%, 93%, 94%, 95%, 96%, 97%, 98%, 99%, or 100%). One of skill will recognize that some variability will arise depending on the method and/or threshold of determining binding.

The term "specifically binds to" or "specifically interacts with" refers to a probe (e.g., an oligonucleotide or an antibody) that binds to a target molecule with at least 2-fold greater affinity than non-target molecules, e.g., at least 4-fold, 5-fold, 6-fold, 7-fold, 8-fold, 9-fold, 10-fold, 20-fold, 25-fold, 50-fold, or 100-fold greater affinity. For example, a probe that specifically binds a particular target molecule will typically bind the target molecule with at least a 2-fold greater affinity than a non-target molecule.

The terms "label" and "detectable label" interchangeably refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, enzymes, biotin, digoxigenin, or haptens and proteins, nucleic acids, or other entities which may be made detectable, e.g, by incorporating a radiolabel into an oligonucleotide, peptide, or antibody specifically reactive with a target molecule. Any method known in the art for conjugating, e.g., for conjugating a probe to a label, may be employed, e.g., using methods described in Hermanson, Bioconjugate Techniques 1996, Academic Press, Inc., San Diego.

A molecule that is "linked" to a label (e.g., as for a labeled probe as described herein) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

DETAILED DESCRIPTION OF THE INVENTION

I. Introduction

The present invention provides methods, compositions, and kits for detecting one or more target molecules in a sample. In a related aspect, the present invention provides methods, compositions, and kits for detecting a complex of target molecules or interactions between two or more target molecules in a sample. Samples are incubated with two, three, four, five, or more probes that specifically bind to a target molecule or target molecules that may be present in the sample. The samples are partitioned into a number of partitions and analyzed for the presence or absence of the labeled probes, e.g., using digital analysis. In some embodiments, the signal or signals generated by the labeled probes are amplified before they are detected. The methods described herein allow for improved sensitivity of detecting a target molecule or molecules and precise quantification of the target molecule or molecules, and lower the limits of direct detection of target molecules in a sample.

II. Detection of a Target Molecule by Co-Localizing Probes

Figure 1:
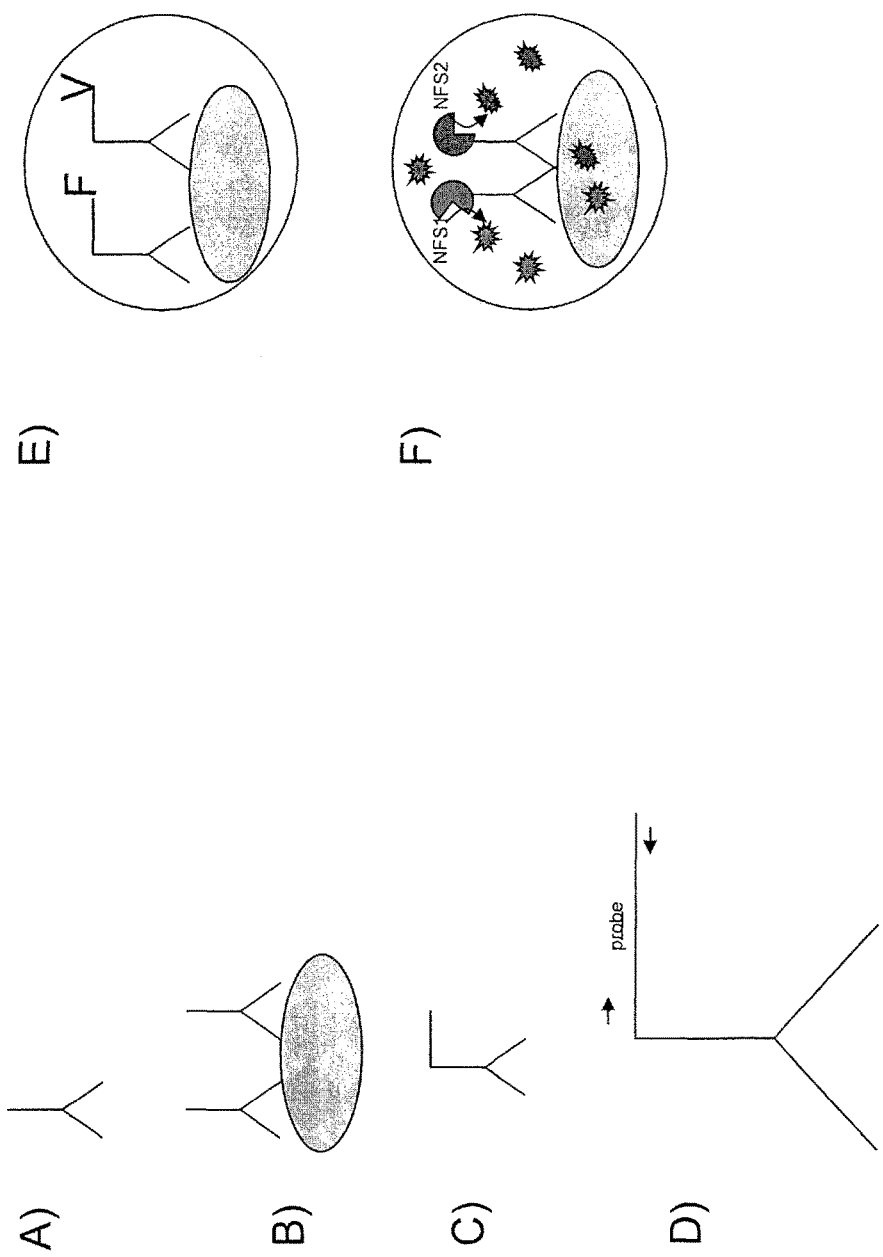
FIG. 1. Legend for schematics in FIGS. 2-4, 6, and 7. (A) Representation of probes for binding to a target molecule (e.g., antibody, aptamer, etc.). (B) Two probes binding to a target molecule (e.g., antibodies recognizing different epitopes on the target molecule). (C) Probe with a nucleic acid strand (label) linked. (D) Detail of antibody (probe) with nucleic acid strand (label) linked and indicating primers and probe for amplifying signal from the label. (E) Partition (droplet) containing two antibodies binding to different epitopes of the target molecule; one antibody is labeled with an oligo detectable by a FAM-based assay (denoted by F) and the other antibody is labeled with an oligo detectable by a VIC-based assay (denoted by V). (F) Partition (droplet) containing two probes binding to different epitopes of the target molecule and labeled with fluorescent labels that generate signal by enzymatic cleavage of a non-fluorescent substrate (NFS) into a detectable marker.
Figure 2:
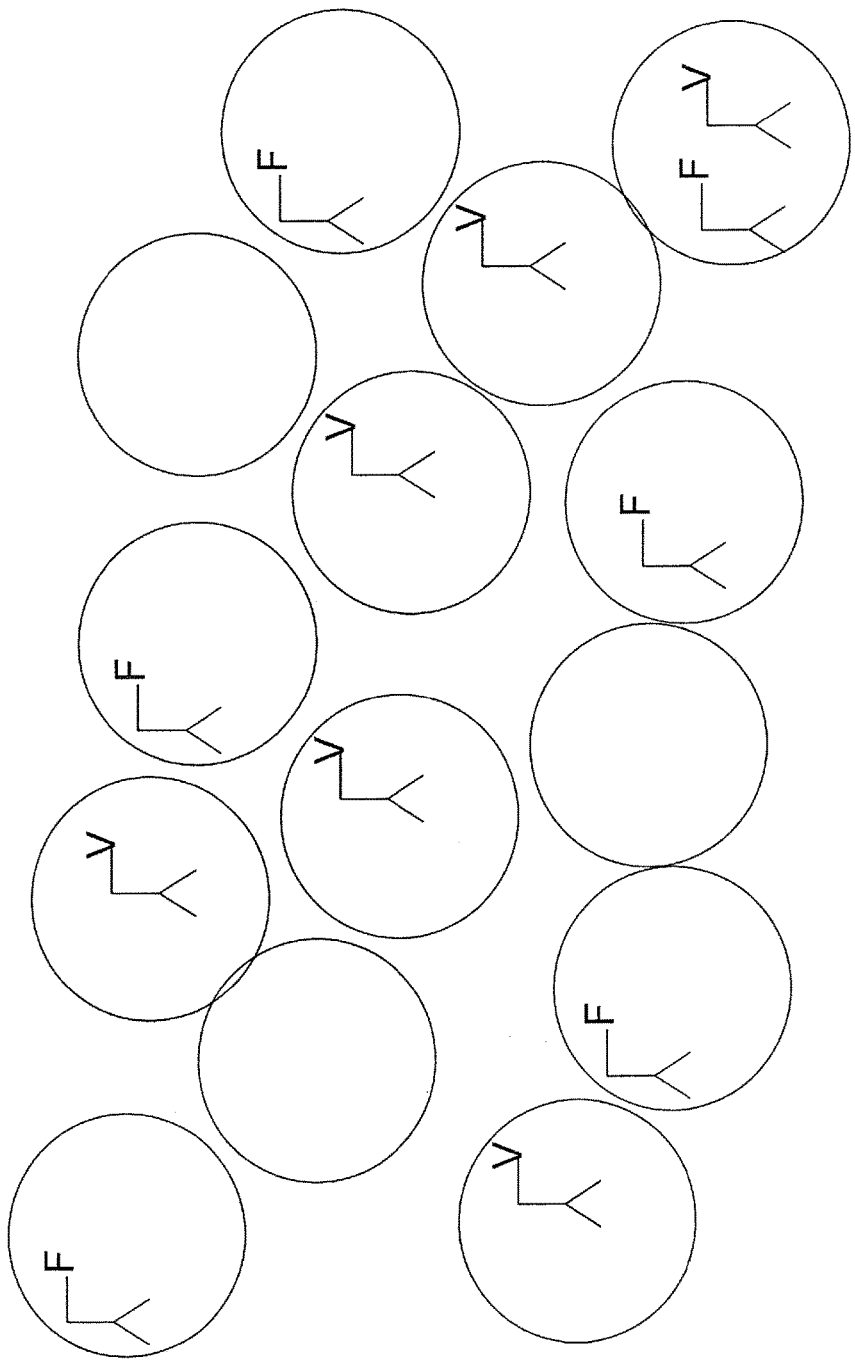
FIG. 2. Schematic of probe partitioning without target molecule present. Antibodies segregate among partitions largely due to random chance, and detection of the antibodies by fluorescent signal shows that the probes rarely co-localize.
Figure 3:
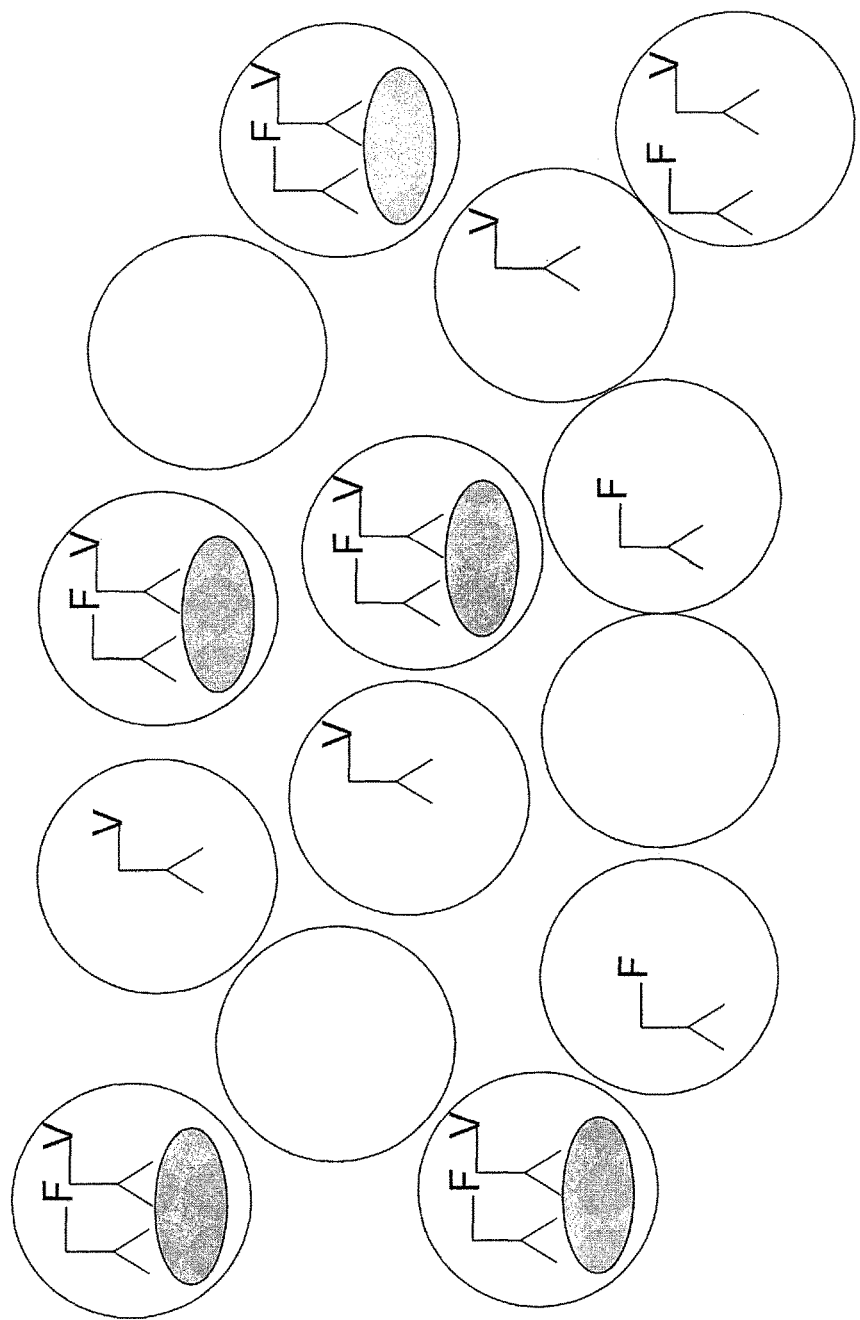
FIG. 3. Schematic of probe partitioning with target molecules present. Antibodies partition non-randomly due to the presence of target molecules. The presence of antibodies is detected due to the associated fluorescent signal.

In one aspect, the present invention relates to methods of detecting a target molecule in a sample using two or more probes that co-localize to the target molecule. Without being bound to a particular theory, it is believed that when a sample is highly partitioned to have a small number of probe molecules per partition (e.g., on average fewer than about 5, 4, 3, 2, or 1 probes per partition), the likelihood that multiple different probes will co-localize to a particular partition by chance, rather than by specific binding to a target molecule in the partition, can be calculated. Binding of multiple different probes to a target molecule results in co-localization of the probes due to their forced physical proximity. The presence of target molecules increases the rate of co-localization. See FIGS. 2 and 3. Thus, for a sample that is partitioned to have a small number of probe molecules per partition, the abundance of co-localization of two or more probes in partitions can be used to calculate the concentration of a target molecule.

In some embodiments, the method comprises:
incubating a sample with two or more probes (e.g., a first probe and a second probe), wherein the two or more probes (e.g., the first probe and the second probe) specifically bind to the same target molecule, if present;
partitioning the sample into two or more partitions; and
detecting the presence of the two or more probes (e.g., the first probe and the second probe) in at least one same partition; thereby detecting the target molecule in the sample.

In some embodiments, the method comprises incubating the sample in a mixture with the two or more probes (e.g., the first probe and the second probe) under conditions suitable for specifically binding the two or more probes to the one or more target molecules. In some embodiments, the method comprises incubating a sample with two or more probes, wherein each probe is linked to a label (e.g., a first probe linked to a first label, a second probe linked to a second label, etc.) and detecting the presence of the two or more labels (e.g., the first label and the second label) in at least one same partition. Suitable conditions for specifically binding the two or more probes to the one or more target molecules will depend on the nature of the probes and target molecules and can be readily determined by a person of skill in the art.

Probes

A probe suitable for use according to the methods described herein is any molecule that specifically interacts with or specifically binds to a target molecule. The methods of the present invention utilize two or more probes (e.g., 2, 3, 4, 5, or more probes). In some embodiments, each of the two or more probes specifically bind to the same target molecule to non-overlapping or partially overlapping regions of the target molecule.

In some embodiments, the 2, 3, 4, 5, or more probes are the same type of molecule (e.g., all antibodies). In some embodiments, at least two of the 2, 3, 4, 5 or more probes are the same type of molecule (e.g., at least two are antibodies). In some embodiments, the 2, 3, 4, 5, or more probes are different types of molecules (e.g., an antibody and a nucleic acid).

In some embodiments, the probe is a peptide, polypeptide, or protein. As used herein, the terms "peptide," "polypeptide," and "protein" interchangeably refer to a polymer of two or more amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. In some embodiments, the probe is an antibody. As used herein, "antibody" refers to a polypeptide of the immunoglobulin family or a polypeptide comprising fragments of an immunoglobulin that is capable of noncovalently, reversibly, and in a specific manner binding a corresponding antigen. The term antibody also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)). Methods for the preparation of antibodies are known in the art; see, e.g., Kohler & Milstein, *Nature* 256:495-497 (1975); Kozbor et al., *Immunology Today* 4:72 (1983); Cole et al., Monoclonal Antibodies and Cancer Therapy, pp. 77-96. Alan R. Liss, Inc. 1985). In some embodiments, the probe is a non-antibody protein scaffold. As used herein, a "non-antibody protein scaffold" refers to a non-immunogenic polypeptide that is capable of binding to a target molecule with high specificity. In some embodiments, the protein scaffold has a structure derived from protein A, a lipocalin, a fibronectin domain, an ankyrin consensus repeat domain, or thioredoxin. Methods of preparing non-antibody scaffolds are known in the art; see, e.g., Binz and Pluckthun, *Curr Opin Biotechnol* 16:459-469 (2005); Koide et al., *J Mol Biol* 415:393-405 (2012); and Gilbreth and Koide, *Curr Opin Struct Biol* 22:413-420 (2012).

In some embodiments, the probe is a nucleic acid. As used herein, the terms "nucleic acid" and "polynucleotide" interchangeably refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Methods of synthesizing polynucleotides are known in the art. See, e.g., Carruthers et al., Cold Spring Harbor Symp. *Quant. Biol.* 47:411-418 (1982), and Adams et al., *J. Am. Chem. Soc.* 105:661 (1983). In some embodiments, the probe is an oligonucleotide that hybridizes to a target molecule. In some embodiments, an oligonucleotide probe is at least 5, 10, 15, 20, 25, 30, 35, 40, 45, 50, 60, 70, 80, 90, 100, 200, 300, 400, 500, 600, 700, 800, 900, 1000, 1500, 2000, 2500, 3000, 3500, 4000, 4500, 5000, or more nucleotides in length.

In some embodiments, the probe is an aptamer. An "aptamer," as used herein, refers to a DNA or RNA molecule that has a specific binding affinity for a target molecule, such as a protein or nucleic acid. In some embodiments, aptamers are selected from random pools based on their ability to bind other molecules with high affinity specificity based on non-Watson and Crick interactions with the target molecule (see, e.g., Cox and Ellington, *Bioorg. Med. Chem.* 9:2525-2531 (2001); Lee et al., *Nuc. Acids Res.* 32:D95-D100 (2004)). For example, aptamers can be selected using a selection process known as Systematic Evolution of Ligands by Exponential Enrichment (SELEX). See, e.g., Gold et al., U.S. Pat. No. 5,270,163. Aptamers can be selected which bind, for example, nucleic acids, proteins, small organic compounds, vitamins, or inorganic compounds.

Samples

The methods of the present invention can be used to detect one or more target molecules in any type of sample. In some embodiments, the sample is a biological sample. Biological samples can be obtained from any biological organism, e.g., an animal, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc.

In some embodiments, the one or more target molecules to be detected are peptides, proteins (e.g., antibodies, enzymes, growth regulators, clotting factors, or phosphoproteins), polynucleotides (e.g., DNA, such as dsDNA or ssDNA; RNA, such as mRNA or miRNA; or DNA-RNA hybrids), aptamers, immunogens, peptide nucleic acids, viruses, virus-like particles, polysaccharides, carbohydrates, lipids, toxins (e.g., viral or bacterial toxins), microorganisms, drug compounds, metabolites, or cells. In some embodiments, the target molecule to be detected is a protein. In some embodiments, the target molecule to be detected is an RNA, e.g., an mRNA or an miRNA.

In some embodiments, two, three, four, five, or more different target molecules are to be detected. In some embodiments, wherein two or more different target molecules are to be detected, the two or more different molecules are the same type of molecule (e.g., two or more proteins present in a complex). In some embodiments, wherein two or more different target molecules are to be detected, the two or more different molecules are different types of molecules (e.g., a drug compound interacting with a protein).

The number of copies of the target molecule in a sample to be analyzed can be 0, or about or at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 2000, 3000, 4000, 5000, 6000, 7000, 8000, 9000, 10,000, 20,000, 30,000, 40,000, or 50,000. In some embodiments, the sample comprises a low concentration and/or copy number of the one or more target molecules.

In some embodiments, the sample can be prepared to improve the efficient detection of the target molecule or target molecules. For example, in some embodiments the sample can be fragmented, fractionated, homogenized, or sonicated. In some embodiments, a target molecule or molecules of interest, or a sub-fraction comprising the target molecule or molecules of interest, can be extracted or isolated from a sample (e.g., a biological sample). In some embodiments, the sample is enriched for the presence of the one or more target molecules. In some embodiments, the target molecule is enriched in the sample by an affinity method, e.g., immunoaffinity enrichment. In some embodiments, the target molecule is enriched in the sample using size selection (e.g., removing very small fragments or molecules or very long fragments or molecules).

In some embodiments, the sample is incubated with the two or more probes prior to partitioning the sample. In some embodiments, the two or more probes are present in a mixture. The mixture comprising the two or more probes can include one or more buffers (e.g., aqueous buffers) and optionally one or more additives (e.g., blocking agents or biopreservatives).

As described below, in some embodiments, each of the two or more probes is designed to specifically bind to the same target molecule (e.g., at distinct locations on the target molecule), if present. In some embodiments, the two or more probes are designed to specifically bind to different target molecules, if present, wherein the target molecules form a complex or interact with each other (e.g., receptor-ligand, drug-effector, etc.). The sample is incubated with the two or more probes (e.g., in a mixture with the two or more probes) under conditions suitable for specifically binding the two or more probes to the one or more target molecules.

In some embodiments, wherein the sample comprising the target molecule is incubated with the two or more probes, the activity of the probes is inhibited prior to the partitioning of the sample. For example, in some embodiments, wherein the sample is incubated with a first enzyme and a second enzyme, the activity of the first and second enzymes is inhibited prior to the partitioning.

In some embodiments, after a sample is incubated with two or more probes under conditions suitable for specifically binding the two or more probes to one or more target molecules, the sample is washed to remove probes that do not specifically bind to their target molecules. In some embodiments, a sample is incubated with a first probe, then optionally subjected to wash conditions before incubating the sample with a second probe. In some embodiments, serially incubating a sample with a probe, then optionally subjecting the sample to wash conditions, then incubating a sample with a different probe can be performed for two, three, four, or five probes or more.

The selection of appropriate wash conditions, wash buffers, etc. will vary based upon conditions such as probe, target molecule, etc., and can be determined by a person skilled in the art. For example, in some embodiments, wherein the probe-target complex is denser than the probe alone, the sample can be washed by centrifugation to pellet the probe-target molecule complex, followed by resuspension in a buffer lacking probe. As another example, in some embodiments, a probe-target molecule complex can be separated from unbound probe by passing the sample through a density gradient or other gradient (e.g., separation by charge). As another example, in some embodiments, a probe-target molecule complex can be washed by passing the sample through a column (e.g., size exclusion column) to separate the complex from unbound probe. A wash process can be repeated for additional washes as necessary. In some embodiments, the sample is washed before partitioning. In some embodiments, the sample is washed after partitioning. In some embodiments, no intervening wash step is performed after incubation of the sample with the probes and before detection of the probes.

In some embodiments, the sample is maintained at a controlled temperature or range of temperatures before, during, and/or after partitioning the sample. In some embodiments, the sample is maintained at a temperature of about 20°, 25°, 30°, 35°, 40°, 45°, 50°, 55°, 60°, 65°, 70°, 75°, 80°, 85°, 90°, or 95° C. before, during, and/or after partitioning the sample, e.g., at a temperature to allow for amplification of signal generated by one or more labeled probes.

Detectable Labels

The probes described herein are detected by detecting a label that is linked to each of the probes. The label can be linked directly to the probe (e.g., by a covalent bond) or the attachment can be indirect (e.g., using a chelator or linker molecule). The terms "label" and "detectable label" are used synonymously herein. In some embodiments, each probe label (e.g., a first label linked to a first probe, a second label linked to a second probe, etc.) generates a detectable signal and the signals (e.g., a first signal generated by the first label, a second signal generated by the second label, etc.) are distinguishable. In some embodiments, the two or more probe labels comprise the same type of agent (e.g., a first label that is a first fluorescent agent and a second label that is a second fluorescent agent). In some embodiments, the two or more probe labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more probes used for detecting a target molecule are each labeled with an optical agent such as a fluorescent agent (e.g., a first probe labeled with a first fluorescent label, a second probe labeled with a second fluorescent label, etc.), and each probe that is labeled with an optical agent is detected by detecting a signal generated by the optical agent (e.g., a fluorescent signal generated by a fluorescent label). In some embodiments, all of the probes used for detecting a target molecule are labeled with an optical agent, and each optical agent-labeled probe is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, 2, 3, 4, 5, or more probes used for detecting a target molecule are each labeled with a radioisotope (e.g., a first probe labeled with a first radioisotope, a second probe labeled with a second radioisotope, etc.), and each probe that is labeled with a radioisotope is detected by detecting radioactivity generated by the radioisotope. In some embodiments, all of the probes used for detecting a target molecule are labeled with a radioisotope and each labeled probe is detected by detecting radioactivity generated by the radioisotope.

Figure 4:
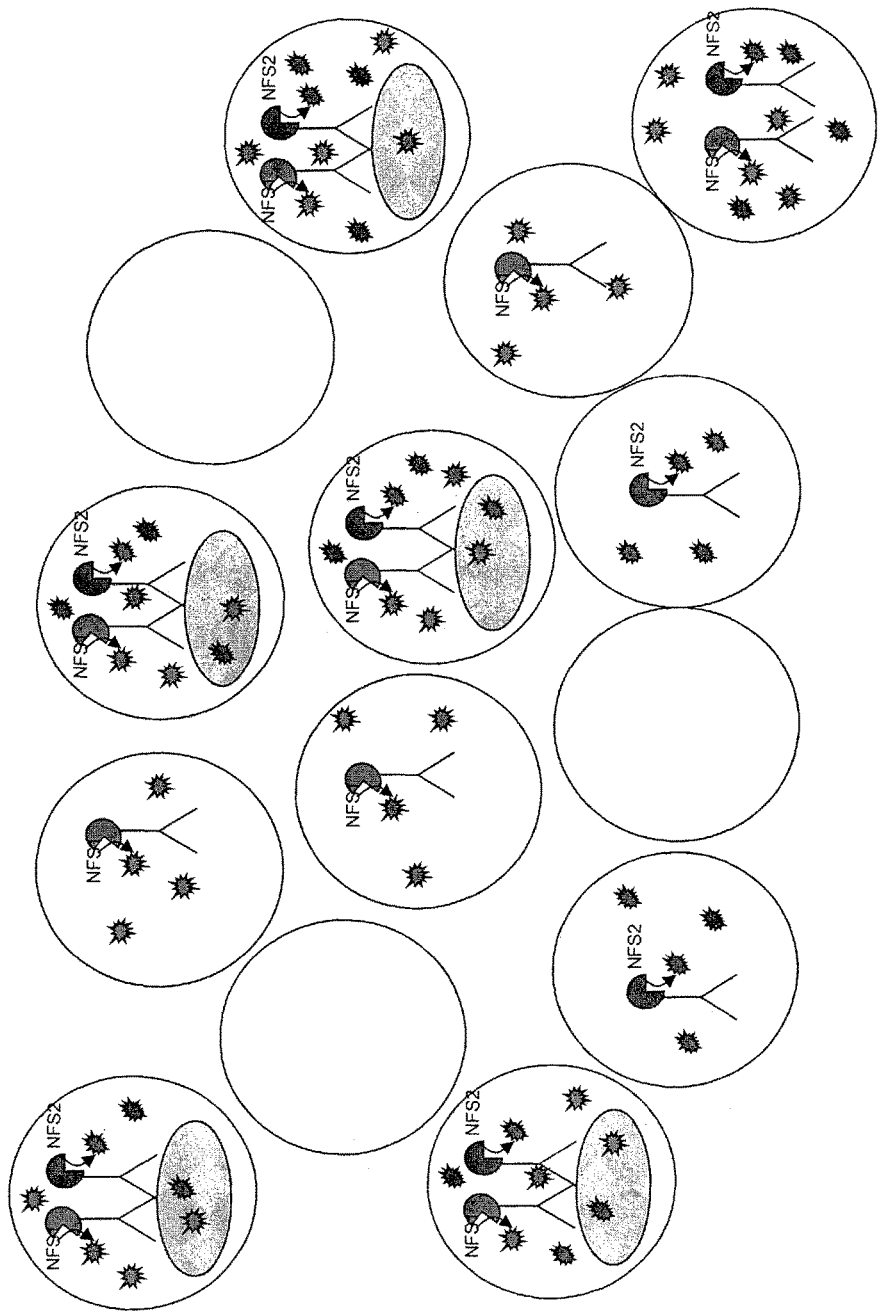
FIG. 4. Schematic of probe partitioning with target molecules present. Probes partition non-randomly due to the presence of target molecules. The presence of antibodies is detected due to the associated fluorescent signal generated by enzymatic cleavage of a non-fluorescent substrate.

In some embodiments, the label is an enzyme, and the probe is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more probes used for detecting a target molecule are each labeled with an enzyme (e.g., a first probe labeled with a first enzyme, a second probe labeled with a second enzyme, etc.), and each probe that is labeled with an enzyme is detected by detecting a product generated by the enzyme. In some embodiments, all of the probes used for detecting a target molecule are labeled with an enzyme, and each enzyme-labeled probe is detected by detecting a product generated by the enzyme. See FIG. 4.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectably labeled (e.g., a fluorescently labeled, biotinylated, or radiolabeled alkyne or azide moiety).

Techniques for attaching detectable labels to probes are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

Figure 6:
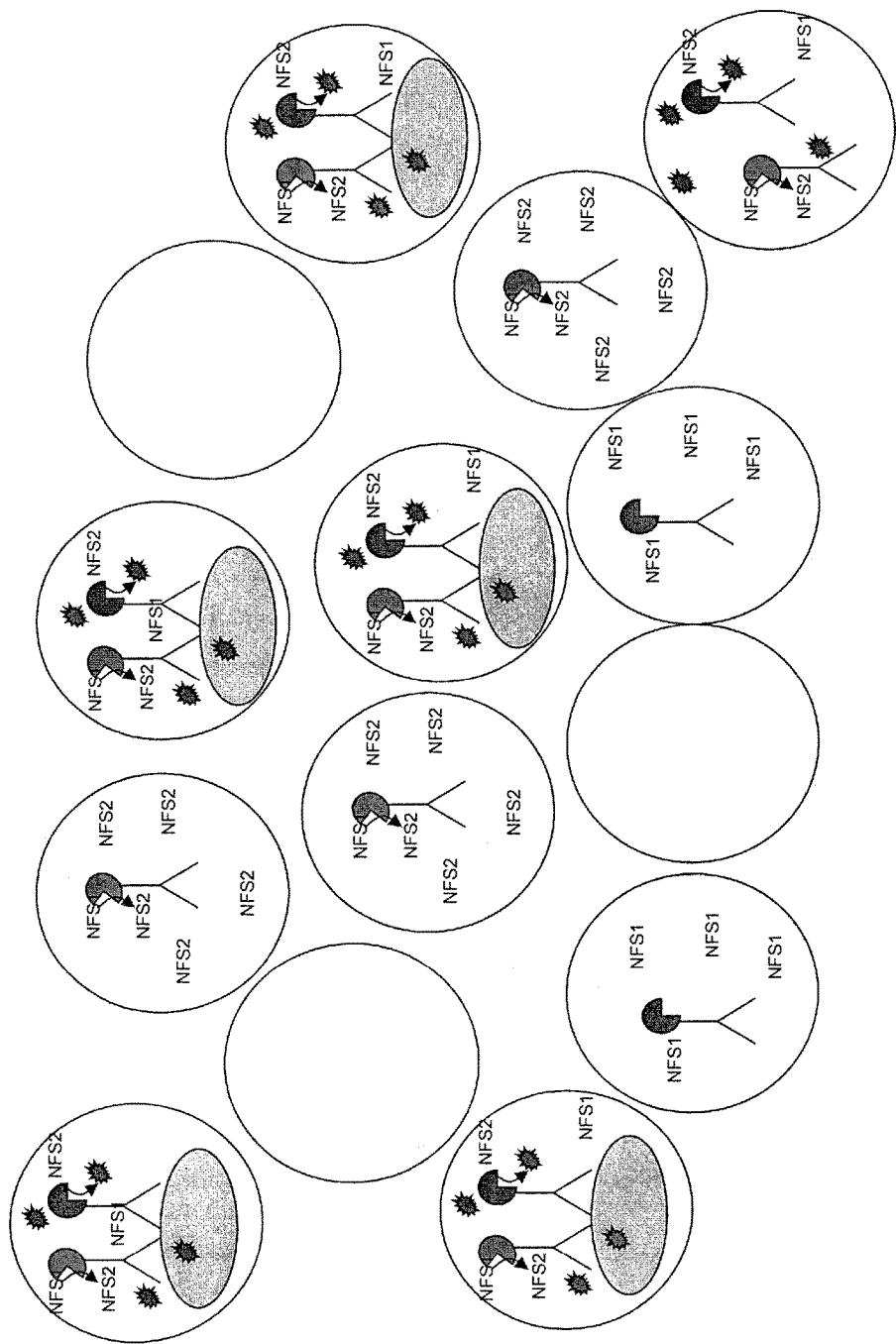
FIG. 6. Probes partition non-randomly due to the presence of target molecules. The presence of both probes is detected due to the signal generated by both conversion reactions (enzymatic cleavage of a non-fluorescent substrate (NFS) into a detectable marker) happening within one partition.

In some embodiments, two or more probe labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of the probes specifically binding the target molecule). See FIG. 6. Examples of enzymes combining to generate a detectable signal include coupled assays, such as a coupled assay using hexokinase and glucose-6-phosphate dehydrogenase; and a chemiluminescent assay for NAD(P)H coupled to a glucose-6-phosphate dehydrogenase, beta-D-galactosidase, or alkaline phosphatase assay. See, e.g., Maeda et al., *J Biolumin Chemilumin* 1989, 4:140-148.

Detection

A detectable label can be detected using any of a variety of detector devices. Exemplary detection methods include radioactive detection, optical absorbance detection (e.g., fluorescence or chemiluminescence), or mass spectral detection. As a non-limiting example, a fluorescent label can be detected using a detector device equipped with a module to generate excitation light that can be absorbed by a fluorescer, as well as a module to detect light emitted by the fluorescer.

In some embodiments, detectable labels in partitioned samples can be detected in bulk. For example, partitioned samples (e.g., droplets) can be partitioned into one or more wells of a plate, such as a 96-well or 384-well plate, and the signal(s) (e.g., fluorescent signal(s)) may be detected using a plate reader.

In some embodiments, the detector further comprises handling capabilities for the partitioned samples (e.g., droplets), with individual partitioned samples entering the detector, undergoing detection, and then exiting the detector. In some embodiments, partitioned samples (e.g., droplets) may be detected serially while the partitioned samples are flowing. In some embodiments, partitioned samples (e.g., droplets) are arrayed on a surface and a detector moves relative to the surface, detecting signal(s) at each position containing a single partition. Examples of detectors are provided in WO 2010/036352, the contents of which are incorporated herein by reference. In some embodiments, detectable labels in partitioned samples can be detected serially without flowing the partitioned samples (e.g., using a chamber slide).

Following acquisition of fluorescence detection data, a general purpose computer system (referred to herein as a "host computer") can be used to store and process the data. A computer-executable logic can be employed to perform such functions as subtraction of background signal, assignment of target and/or reference sequences, and quantification of the data. A host computer can be useful for displaying, storing, retrieving, or calculating diagnostic results from the molecular profiling; storing, retrieving, or calculating raw data from expression analysis; or displaying, storing, retrieving, or calculating any sample or patient information useful in the methods of the present invention.

The host computer may be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, may be included. Where the host computer is attached to a network, the connections may be provided via any suitable transport media (e.g., wired, optical, and/or wireless media) and any suitable communication protocol (e.g., TCP/IP); the host computer may include suitable networking hardware (e.g., modem, Ethernet card, WiFi card). The host computer may implement any of a variety of operating systems, including UNIX, Linux, Microsoft Windows, MacOS, or any other operating system.

Computer code for implementing aspects of the present invention may be written in a variety of languages, including PERL, C, C++, Java, JavaScript, VBScript, AWK, or any other scripting or programming language that can be executed on the host computer or that can be compiled to execute on the host computer. Code may also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface may be provided, allowing the user to control operations using a pointing device. Thus, the present invention is not limited to any particular user interface.

Scripts or programs incorporating various features of the present invention may be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

III. Detection without Target Amplification

In another aspect of the present invention, the target molecule is detected and quantified without amplification of the target molecule ("target amplification"). Avoiding target amplification eliminates problems and inaccuracies that may result from amplification, such as sensitivity to PCR inhibitors, contamination concerns, and the recovery of the original template from copies that are made during amplification.

In some embodiments, the target molecule is detected by detecting the signal or signals generated by the labeled probes that bind to the target molecule without amplifying the signal or signals generated by the labeled probes. Examples of labels that can be detected without amplification of the signal include, but are not limited to, fluorophores, intercalating dyes or agents, mass labels, and molecular beacon oligonucleotides. In some embodiments, at least one of the labeled probes that binds to a target molecule is detected without amplifying the signal generated by the labeled probe. In some embodiments, all of the labeled probes that bind to a target molecule are detected without amplifying the signal generated by the labeled probe.

In some embodiments, the target molecule is directly detected using a fluorophore. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995). Non-limiting examples of fluorophores include cyanines, fluoresceins (e.g., 5'-carboxyfluorescein (FAM), Oregon Green, and Alexa 488), rhodamines (e.g., N,N,N',N'-tetramethyl-6-carboxyrhodamine (TAMRA), tetramethyl rhodamine, and tetramethyl rhodamine isothiocyanate (TRITC)), eosin, coumarins, pyrenes, tetrapyrroles, arylmethines, oxazines, polymer dots, and quantum dots.

In some embodiments, the target molecule is directly detected using a mass label (molecular mass label) that can be detected using mass spectrometry. Mass labels are commercially available, e.g., Thermo Fisher Tandem Mass Tag (TMT).

In some embodiments, the target molecule is directly detected using an intercalating agent. Intercalating agents produce a signal when intercalated in double stranded DNA. Exemplary agents include SYBR GREEN™, SYBR GOLD™, and EVAGREEN™.

In some embodiments, the target molecule is directly detected using a molecular beacon oligonucleotide probe. The "beacon probe" method (described by Tyagi and Kramer, *Nature Biotech.* 14:303-309 (1996), which is also the subject of U.S. Pat. Nos. 5,119,801 and 5,312,728) relies on the use of energy transfer. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched.

Signal Amplification

In some embodiments, the signal or signals generated by the labeled probes are amplified ("signal amplification") before they are detected. Signal amplification can increase the intensity of a signal and thus improve target molecule detection, but without introducing the problems that can result from amplifying a target molecule to be detected. In some embodiments, signals generated by a labeled probe are amplified by an enzymatic reaction (e.g., a chromogenic reaction), by a nucleic acid amplification reaction that amplifies the labeled probe rather than the target molecule, by branched DNA, or by an invader assay.

In some embodiments, signals generated by one or more labeled probes are amplified by a nucleic acid amplification reaction (e.g., polymerase chain reaction (PCR), quantitative PCR (qPCR), or ligase chain reaction (LCR)). In some embodiments, one or more probes is labeled with a nucleic acid label. The one or more labels are amplified to generate an amplicon and the detecting comprises detecting the amplicon. In some embodiments, the signal amplification method is immuno-PCR. Immuno-PCR is described, for example, in Niemeyer et al., *Trends Biotechnol.* 2005; 23:208-216. In immuno-PCR, an antibody probe that specifically binds to a target molecule is labeled with a nucleic acid label (e.g., oligonucleotide), and the nucleic acid label is amplified by PCR to generate an amplified signal. In some embodiments, one or more of the primers used to amplify the nucleic acid label is fluorescently labeled. The amplified signal can then be detected and quantified. The nucleic acid label can comprise a detectable tag or label as described herein, e.g., a fluorescent agent such as a TaqMan® probe, for detection of the amplified signal. In some embodiments, each of the two or more probes is an oligonucleotide-labeled antibody that is capable of specifically binding to a target molecule, and each oligonucleotide-labeled antibody is labeled with a different agent, e.g., a different fluorescent agent. Detection of both of the probes in the same partition indicates that the partition is positive for the presence of the target molecule.

In some embodiments, the signal amplification method is proximity ligation assay. In a proximity ligation assay, two antibody probes that target different epitopes of the same target molecule are each labeled with "half" of a nucleic acid strand (e.g., by attaching each nucleic acid strand to a secondary antibody that binds the antibody probe). When the antibody probes both bind to the target molecule, the antibodies are in close proximity, and the two "halves" of the nucleic acid label can be ligated together to make a full-length nucleic acid product that can then be amplified and detected, e.g., by qPCR. The nucleic acid label can comprise a detectable tag or label as described herein, e.g., a fluorescent agent such as a TaqMan® probe, for detection of the amplified signal. Because the antibody probes are unlikely to bind in close proximity to each other in non-specific binding, background signal is expected to be low for such an assay.

In some embodiments, signals generated by one or more labeled probes are amplified by an enzymatic reaction. As described above, a number of enzymatic assays are known that amplify signal to yield a detectable product, e.g., a fluorescent, chemiluminescent, or colorimetric product. Examples of suitable enzymes for signal amplification include, but are not limited to, urease, alkaline phosphatase, horseradish peroxidase (HRP), glucose oxidase, β-galactosidase, luciferase, tyramide signaling amplification (TSA™, PerkinElmer Inc., Santa Clara, Calif.), and an esterase that hydrolyzes fluorescein diacetate. As a non-limiting example, an HRP assay can be used for detecting a labeled probe (e.g., biotin, DIG, or fluorescein labeled probe). The HRP enzyme reagent, which is typically conjugated to an antibody or streptavidin, is incubated with the sample comprising the labeled probe and with an HRP substrate under conditions suitable for the generation of a detectable signal. A variety of fluorescent, chemiluminescent, or colorimetric HRP substrates are known in the art, such as TMB, DAB, and ABTS.

In some embodiments, signals generated by one or more labeled probes are amplified by branched DNA or DNA dendrimers. Generally, in branched DNA signal amplification, one end of a branched DNA molecule is designed to bind a target (e.g., a DNA or RNA sequence) while the other end contains many branches of DNA that can bind a probe for signal detection. Branched DNA is described, for example, in Collins et al., *Nucleic Acids Res* 1997; 25:2979-2984; and in Tsongalis, *Am J Clin Pathol* 2006; 126:448-453.

In some embodiments, signals generated by one or more labeled probes are amplified using an invader assay. Generally, in an invader assay a target-specific oligonucleotide probe and an "invader" oligonucleotide probe hybridize to the target molecule (e.g., target DNA sequence) to form a specific overlapping structure. The target-specific probe contains a "flap" sequence that does not hybridize the target sequence. A cleavage enzyme (e.g., an endonuclease) recognizes the overlapping structure and cleaves the flap of the target-specific probe only when the probes hybridize perfectly. The assay comprises two set of target-specific probe and invader probe. Signal is amplified from the cleaved flaps of the target-specific probes, for example using fluorescent resonance energy transfer (FRET). Invader assays are known in the art and are described, e.g., in U.S. Pat. No. 6,865,572.

One of skill in the art will recognize that the level of signal amplification can vary based on conditions such as reagent concentration, incubation time, and incubation temperature.

IV. Partitioning Samples for Detection

The sample comprising the one or more target molecules to be detected (e.g., a sample incubated with a mixture comprising two or more probes) is partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are microchannels. Methods and compositions for partitioning a sample are described, for example, in published patent applications WO 2010/036352, US 2010/0173394, US 2011/0092373, and US 2011/0092376, the entire content of each of which is incorporated by reference herein.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous sample comprising the target molecule(s) to be detected. In some embodiments, the aqueous sample comprising the target molecule(s) to be detected further comprises a buffered solution and two or more probes for detecting the target molecule(s).

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing.

Following conversion, the microcapsules may be stored at about −70°, −20°, 0°, 3°, 4°, 5°, 6°, 7°, 8°, 9°, 10°, 15°, 20°, 25°, 30°, 35°, or 40° C. In some embodiments, these capsules are useful in biomedical applications, such as stable, digitized encapsulation of macromolecules, particularly aqueous biological fluids comprising a mix of target molecules such as nucleic acids, proteins, or both together; drug and vaccine delivery; biomolecular libraries; clinical imaging applications; and others.

The microcapsule partitions may contain one or more probes (e.g., labeled probes as described herein) and may resist coalescence, particularly at high temperatures. Accordingly, the capsules can be incubated at a very high density (e.g., number of partitions per unit volume). In some embodiments, greater than 100,000, 500,000, 1,000,000, 1,500,000, 2,000,000, 2,500,000, 5,000,000, or 10,000,000 partitions may be incubated per mL. In some embodiments, the sample-probe incubations occur in a single well, e.g., a well of a microtiter plate, without inter-mixing between partitions. The microcapsules may also contain other components necessary for the incubation.

In some embodiments, the sample is partitioned into at least 500 partitions, at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that co-localization of the probes due to binding of a target molecule can be distinguished from random co-localization. In some embodiments, the partitioning comprises generating at least 1 partition that has 0 copies of the target molecule. In some embodiments, the partitioning comprises generating at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 0 copies of the target molecule. In some embodiments, the partitioning comprises generating at least 1 partition that has 0 copies of the target molecule and at least 1 partition that has 1 or more copies (e.g., 1, 2, 3, 4, 5, 6, 7, 8, 9, 10 or more copies) of the target molecule. In some embodiments, the partitioning comprises generating at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 0 copies of the target molecule and at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more that have 1 or more copies (e.g., 1, 2, 3, 4, 5, 6, 7, 8, 9, 10 or more copies) of the target molecule. In some embodiments, the partitioning comprises generating a sufficient number of partitions such that the probes do not co-localize in at least 1 partition. In some embodiments, the partitioning comprises generating a sufficient number of partitions such that the two or more probes do not co-localize in at least 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more.

In some embodiments, the sample is partitioned into a sufficient number of partitions such that at least a majority of partitions have no more than 5 copies of the target molecule (e.g., about 0.5, 1, 2, 3, 4, or 5 copies of the target molecule). In some embodiments, a majority of the partitions have no more than 5 copies of the one or more target molecules to be detected. In some embodiments, on average no more than 5 copies of the one or more target molecules are present in each partition. In some embodiments, on average about 0.5, 1, 2, 3, 4, or 5 copies of the target molecule are present in each partition. In some embodiments, on average about 0.001, 0.005, 0.01, 0.05, 0.1, 0.5, 1, 2, 3, 4, or 5 probes are present in each partition.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

V. Digital Analysis

A digital readout assay, e.g., digital analysis, can be used to count the number of target molecules by partitioning the target molecules in a sample and identifying the partitions containing the target. Generally, the process of digital analysis involves determining for each partition of a sample whether the partition is positive or negative for the presence of the target molecule or target molecules to be detected. For quantifying the amount of target molecule in a sample (e.g., quantifying the concentration or number of copies of a target molecule in a sample), the partitions are examined for the presence of the two or more probes in each partition. A partition is "positive" for the presence of the target molecule if each of the two or more probes that was incubated with the sample is detected in the partition. In some embodiments, each of the two or more probes is detected in the partition by detecting the presence of a signal generated by a label linked to the probe (e.g., a fluorescent, chemiluminescent, radioactive, or enzymatic label linked to the probe), wherein the signals generated by the different labels are distinguishable (e.g., a first label linked to a first probe generates a first signal that is distinguishable from a second signal generated by a second label linked to a second probe). In some embodiments, the two or more probes are detected in the partition by detecting the production of a signal that is generated when both labeled probes are present in the same partition but not in the absence of one or both probes from the same partition. A partition is "negative" for the presence of the target molecule if at least one of the two or more probes that was incubated with the sample is not detected in the partition.

In some embodiments, a detector that is capable of detecting a signal or multiple signals is used to analyze each partition for the presence or absence of the target molecule. For example, in some embodiments a two-color reader (fluorescence detector) is used. The fraction of positive-counted partitions can enable the determination of absolute concentrations for the target molecule to be measured.

Once a binary "yes-no" result has been determined for each of the partitions of the sample, the data for the partitions is analyzed using an algorithm based on Poisson statistics to quantitate the amount of target molecule in the sample. Statistical methods for quantitating the concentration or amount of a target molecule or target molecules is described, for example, in WO 2010/036352, which is incorporated by reference herein in its entirety.

In some embodiments, the concentration of target molecule in a sample can be determined by empirically comparing the rate of co-localization of multiple different probes in the sample to the rate of co-localization of the multiple different probes in a sample or samples having a known concentration of target (including, for example, a sample having 0 target molecules) and subtracting the co-localization events that are due to random co-localization from the total number of co-localization events. In some embodiments, the concentration of target molecules or target molecules in a sample can be mathematically calculated as described in Example 1 below.

VI. Detection of Target Molecules Linked to or Capable of Generating a Detectable Molecule In still another aspect, the present invention relates to methods of detecting a target molecule in a sample, wherein the target is linked to or is capable of generating a detectable molecule. In some embodiments, the method comprises incubating the sample with at least one probe (e.g., a detectably labeled probe), wherein the probe specifically binds the target molecule, if present; partitioning the mixture into two or more partitions; and detecting the presence of the probe and the detectable molecule in at least one same partition, thereby detecting the target molecule in the sample.

In some embodiments, the method comprises incubating the sample comprising the target that is linked to or is capable of generating a detectable molecule in a mixture with at least one probe (e.g., a first probe) under conditions suitable for specifically binding the probe to the target molecule. In some embodiments, the probe is linked to a detectable label (e.g., a first probe linked to a first label) and the method comprises detecting the presence of the label (e.g., the first label) and the detectable molecule in at least one same partition. Suitable conditions for specifically binding the probe to the target molecule will depend on the nature of the probe and target molecule and can be readily determined by a person of skill in the art.

In some embodiments, the target molecule is linked to or bound by a detectable molecule. In some embodiments, the detectable molecule that is linked to or bound by the target molecule is an optically detectable agent, e.g., a fluorescent agent.

In some embodiments, the target molecule is capable of generating a detectable molecule in the sample. In some embodiments, the target molecule is an enzyme capable of converting a substrate in the mixture into the detectable molecule or converting a substrate in the mixture into an intermediate molecule that is further converted into the detectable molecule by the label that is linked to the probe (e.g., the first label). In some embodiments, the target molecule is a complex of proteins, e.g., an enzyme complex.

In one non-limiting example, the target molecule is an isoform of lactic dehydrogenase (LDH), e.g., LDH1, LDH2, LDH3, LDH4, or LDH5. In some embodiments, the methods as described herein are used to detect the presence of the LDH enzyme as well as the conversion of NAD+ to NADH, due to the activity of LDH enzyme. For example, in some embodiments, the method comprises incubating a sample comprising an LDH isoform in a mixture comprising a labeled antibody probe to LDH and detecting in the same partition the labeled antibody probe and the LDH enzyme conversion product (NADH). In some embodiments, the method comprises incubating a sample comprising an LDH isoform in a mixture comprising a labeled antibody probe to LDH and detecting in the same partition the labeled antibody probe and the activity of LDH through a coupled assay (e.g., using diaphorase, which converts resazurin to the fluorescent molecule resorufin stoichiometrically with the conversion of NADH to NAD+, thus leading to a fluorescent signal in the presence of LDH). In some embodiments, the method comprises incubating a sample comprising an LDH isoform in a mixture comprising a labeled antibody probe to LDH, wherein the antibody is coupled to a coupled assay component for detecting LDH activity (e.g., an antibody coupled to diaphorase) and detecting in the same partition the labeled antibody probe and the activity of LDH through a coupled assay (e.g., a diaphorase assay as described above).

Figure 7:
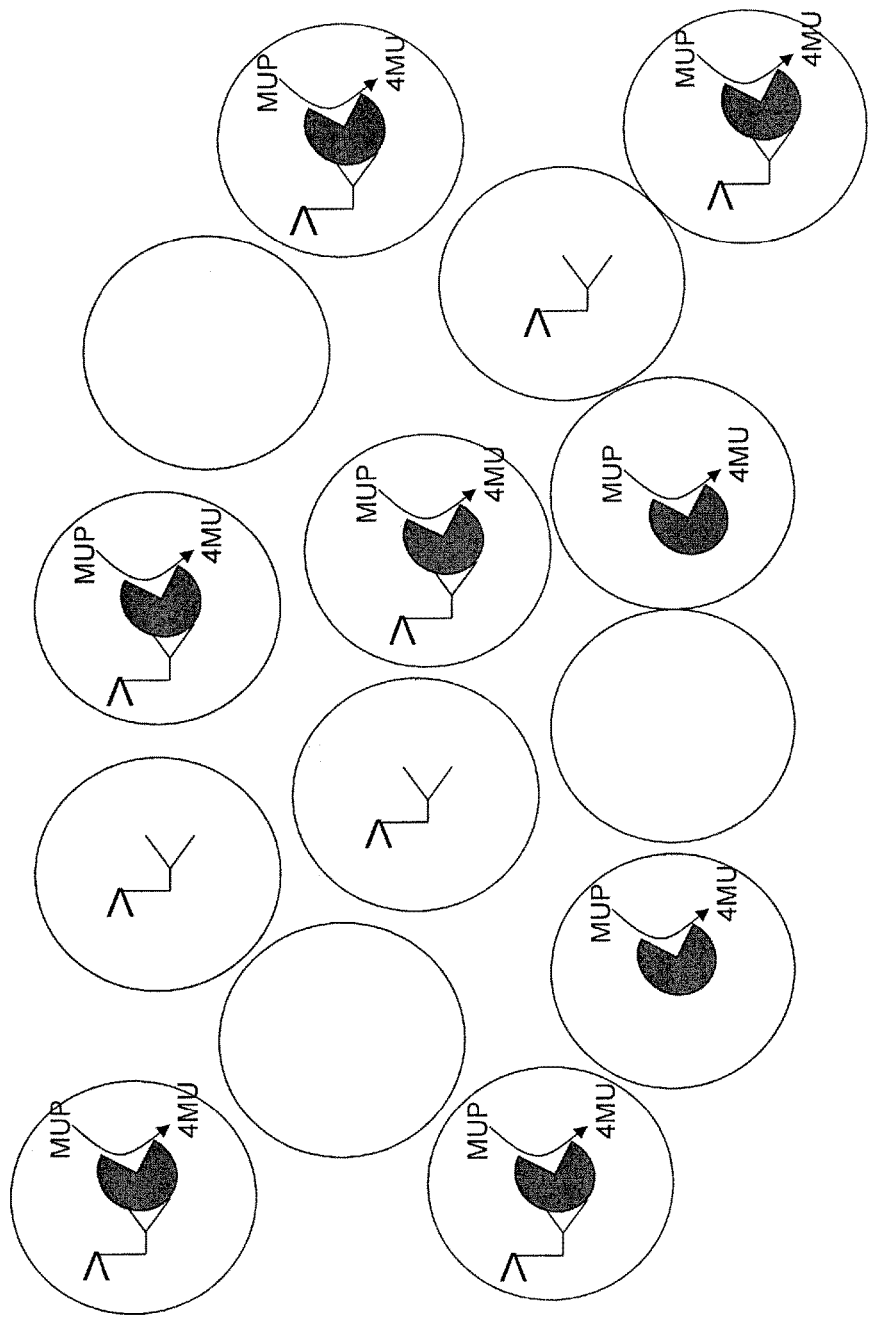
FIG. 7. Detection of intrinsic activity of a target molecule combined with a target-specific probe. In this example, the target molecule is alkaline phosphatase (AP) or a complex comprising AP. Detection of AP activity through conversion of 4-methylumbelliferyl phosphate (MUP) to 4-methylumbelliferone (4MU) is combined with detection of a labeled probe (VIC, "V") with specificity for a particular isoform of AP.

In another non-limiting example, the target molecule is alkaline phosphatase (AP), which converts 4-methylumbelliferyl phosphate (MUP) to 4-methylumbelliferone (4MU), a fluorescent molecule. In some embodiments, the methods as described herein are used to detect the presence of the AP enzyme (e.g., a specific isoform of AP) as well as the conversion of MUP to 4MU. For example, in some embodiments, the method comprises incubating a sample comprising an AP isoform in a mixture comprising a labeled antibody probe to AP and detecting in the same partition the labeled antibody probe and the AP enzyme conversion product (4MU). See FIG. 7.

In another non-limiting example, the target molecule is an enzyme complex, e.g., a complex of an LDH isoform and IgG. LDH-IgG isoforms can be indicative of LDH anomalies of clinical significance. The enzyme complex can be detected using a combination of labeled probes (e.g., a labeled antibody probes against IgG) and detection of the activity of the enzyme or enzyme complex (e.g., a coupled assay to detect LDH activity as described above).

VII. Detection of Molecular Interactions

In another aspect, the present invention relates to methods of detecting a complex of target molecules or interactions between two or more target molecules in a sample. Without being bound to a particular theory, it is believed that when a sample is highly partitioned to have a small number of probe molecules per partition, the likelihood that multiple different probes will co-localize to a particular partition by chance, rather than by specific binding to a target molecule in the partition, can be calculated. Binding of multiple different probes to a complex of target molecules or to interacting target molecules results in co-localization of the probes due to their forced physical proximity. The presence of target molecules increases the rate of co-localization. Thus, for a highly partitioned sample the abundance of co-localization of two or more probes in partitions can be used to determine the extent of target molecule complexation or target molecule interaction.

In some embodiments, the method of detecting interaction between at least a first target molecule and a second target molecule in a sample comprises:

incubating the sample with at least a first probe that specifically binds the first target molecule, if present, and a second probe that specifically binds the second target molecule, if present;

partitioning the sample into two or more partitions; and detecting the presence of the first probe and the second probe in at least one same partition; thereby detecting the interaction between the first target molecule and the second target molecule in the sample.

The target molecule interaction or target molecule complex to be detected can be any interaction between or complex of any two or more target molecules as described herein (e.g., any peptide, protein, polynucleotide, aptamer, peptide nucleic acid, carbohydrate, virus, virus-like particle, drug compound, metabolite, or cell). The two or more target molecules can be the same type of molecule (e.g., two proteins) or can be different types of molecules (e.g., a protein and a drug compound or a protein and a small molecule). In some embodiments, the molecular interaction to be detected is a receptor-ligand interaction. In some embodiments, the molecular interaction to be detected is a drug-effector interaction. In some embodiments, the molecular interaction to be detected is an antibody-antigen interaction. In some embodiments, the molecular interaction to be detected is a cell-cell interaction. In some embodiments, the molecular interaction to be detected is a transcription factor-recognition sequence interaction.

In some embodiments, the method comprises incubating the sample in a mixture with at least the first probe and the second probe under conditions suitable for specifically binding the first probe to the first target molecule and the second probe to the second target molecule. Suitable conditions for specifically binding each probe to each target molecule will depend on the nature of the probes and target molecules and can be readily determined by a person of skill in the art.

In some embodiments, the method comprises detecting 2, 3, 4, 5, or more probes. In some embodiments, the 2, 3, 4, 5, or more probes are the same type of molecule (e.g., all antibodies). In some embodiments, at least two of the 2, 3, 4, 5 or more probes are the same type of molecule (e.g., at least two are antibodies). In some embodiments, the 2, 3, 4, 5, or more probes are different types of molecules (e.g., an antibody and a nucleic acid). Suitable probes for detecting target molecule interactions or complexes include any of the probes described herein, e.g., in Section II above.

In some embodiments, the method comprises incubating a sample with at least the first probe and the second probe, wherein each probe is linked to a label (e.g., a first probe attached to a first label, a second probe linked to a second label, etc.) and detecting the presence of the two or more labels (e.g., the first label and the second label) in at least one same partition. Suitable detectable labels for each of the probes include any of the detectable labels described herein, e.g., in Section II above.

In some embodiments, the first label generates a first signal and the second label generates a second signal and the first signal and the second signal are distinguishable. For example, in some embodiments, the first label is a first enzyme and the second label is a second enzyme, and the detecting comprises detecting products generated by the first and second enzymes. In some embodiments, the first label and the second label combine to produce a signal that is not generated in the absence of the first label, the second label, or both. For example, in some embodiments, the first label is a first enzyme and the second label is a second enzyme and the activities of the first and second enzymes combine to generate a detectable signal indicative of the presence of the first and second labels.

In some embodiments, signals from the first and second labels for detecting target molecule interaction or target molecule complex are directly detected, e.g., using fluorophores, intercalating agents, or mass labels as described herein. In some embodiments, signals from the first and second labels for detecting target molecule interaction or target molecule complex are amplified prior to detection, e.g., by nucleic acid amplification reaction, branched DNA, or enzymatic reaction as described herein.

VIII. Detection of Signal Quenching from Co-Localization

In another aspect, methods are provided for detecting co-localization of two or more probes to a target molecule or to a complex of target molecules by measuring the resulting decrease in signal associated with one or more of the probes. In some embodiments, the method comprises:

incubating a sample in a mixture with at least a first probe linked to a first label and a second probe linked to a second label, wherein the first probe specifically binds to a target molecule, if present in the sample, and wherein the second probe specifically binds to the same target molecule as the first probe or to a second target molecule that interacts with the target molecule that the first probe specifically binds to, if present in the sample;

partitioning the mixture into two or more partitions; and detecting the quenching of a detectable signal generated by the first label and/or the second label in at least one partition; thereby detecting the target molecule or complex of target molecules in the sample.

In some embodiments, the first probe and the second probe both specifically bind to the same target molecule. In some embodiments, the first probe specifically binds to a first target molecule and the second probe specifically binds to a second target molecule. Suitable probes include any of the probes described herein, e.g., in Section II ("Detection of a Target Molecule by Co-Localizing Probes") and/or Section III ("Detection without Target Amplification") above. In some embodiments, the first probe and/or second probe is a nucleic acid (e.g., an oligonucleotide), a protein (e.g., an antibody), an organic compound (e.g., a small molecule effector), or an aptamer.

The probes can be labeled with any detectable label as described herein, e.g., in Section II above. In some embodiments, at least one label is a fluorescent agent. Examples of suitable fluorescent agents that generate a fluorescent signal are described in Section II above. In some embodiments, the second label quenches a fluorescent signal generated by the first label. In some embodiments, the second label is a fluorescent agent, and the first and second labels are members of a fluorescence resonance energy transfer (FRET) pair. The term "fluorescence resonance energy transfer" or "FRET" refers to a transfer of energy between at least two chromophores, a donor chromophore and an acceptor chromophore. Typically in FRET, if the donor and acceptor are in sufficiently close proximity, the donor transfers its energy to the acceptor when the donor is excited by light radiation with a suitable wavelength. The acceptor can re-emit the transferred energy in the form of light radiation with a different wavelength. Suitable FRET pairs (donor/acceptor) include, but are not limited to, EDANS/fluorescein, IAE-DANS/fluorescein, fluorescein/tetramethylrhodamine, fluorescein/LC Red 640, fluorescein/Cy 5, fluorescein/Cy 5.5, and fluorescein/LC Red 705. In some embodiments wherein the first and second labels are a FRET pair, co-localization of two or more probes to a target molecule or complex of target molecules can alternatively or additionally be measured by detecting a signal, or change in signal, generated by the first label and/or a signal generated by the second label in one or more partitions.

In some embodiments, the second label is a nonfluorescent agent that quenches the signal from the first label ("quencher"). In some embodiments, the fluorescent signal generated by the first label is present or relatively increased when the second label (quencher) is not in close proximity to the first label, and the fluorescent signal generated by the first label is absent or relatively decreased when the second label is brought into close proximity with the first label (e.g., by co-localization to a specific epitope on the target molecule). Non-limiting examples of useful quenchers include TAMRA, DABCYL, QSY™ quenchers (e.g., QSY 7 and QSY 21) (Molecular Probes, Eugene, Oreg.), BlackHole Quenchers™ (BHQ) (Biosearch Technologies, Inc., Novato, Calif.), IowaBlack™ (Integrated DNA Tech., Inc., Coralville, Iowa), BlackBerry™ Quencher 650 (BBQ-650) (Berry & Assoc., Dexter, Mich.), paramagnetic ions, and gold nanoparticles. Suitable fluorescent donor/quencher pairs include, but are not limited to, FAM/DABCLY, FAM/TAMRA, EDANS/DABCYL, Texas Red/DABCYL, BODIPY/DABCYL, Lucifer yellow/DABCYL, coumarin/DABCYL, and fluorescein/QSY 7 dye.

In some embodiments, the sample is partitioned into a sufficient number of partitions such that co-localization of the probes due to binding of a target molecule can be distinguished from random co-localization. The sample can be partitioned in any manner as described herein, e.g., in Section IV above.

Reduction in signal (e.g., signal from the first labeled probe), and/or reduction in the number of partitions in which the signal (e.g., signal from the first labeled probe) is present can be determined by detecting the signal according to any of the methods described herein. The number of partitions expressing the signal for a sample of interest can be compared to a control sample (e.g., a sample lacking an agent that quenches the signal from the first probe). In some embodiments, a majority of partitions of the control sample express the signal (e.g., signal from the first labeled probe). In some embodiments, the number of partitions expressing a signal for a sample of interest is "reduced" if the number of partitions expressing the signal is decreased by at least about 1%, 2%, 3%, 4%, 5%, 10%, 15%, 20%, 25%, 30%, 35%, 40%, 45%, 50%, 60%, 70%, 80%, 90% or more as compared to the control sample (e.g., a sample lacking an agent that quenches the signal from the first probe).

In some embodiments, a first target molecule and a second target molecule interact directly. In some embodiments, a first target molecule and a second target molecule interact indirectly, for example, via another molecular component or via a signaling cascase. As a non-limiting example, in a coupled assay with lactic dehydrogenase (LDH), the fluorescent readout is due to the conversion of resazurin to the fluorescent molecule resoruphin stoichiometrically with the conversion of NADH to NAD+, thus leading to a fluorescent signal in the presence of LDH. Thus, the LDH is detected indirectly. Partitions without LDH are negative for resoruphin. Partitions comprising LDH and a first probe resazurin are positive to resoruphin; however, the first probe resazurin is converted to resoruphin by diaphorase rather than LDH. The presence of a second probe, that blocks LDH activity, inhibits NADH formation and thus inhibits signal from resoruphin despite the co-localization of resazurin and LDH, but does so by interacting with LDH and NAD+, not diaphorase, resazurin, or resoruphin.

Sequential Detection

In another aspect, methods are provided for detecting co-localization of two or more probes to a target molecule or to a complex of target molecules by sequentially measuring the resulting decrease in signal associated with one or more of the probes. In some embodiments, the method comprises:

incubating a sample in a mixture with at least a first probe linked to a first label, wherein the first probe specifically binds to a target molecule, if present in the sample;

partitioning the mixture into two or more partitions;

detecting the number of partitions with a detectable signal generated by the first label;

contacting the contents of each partition with a second probe linked to a second label, wherein the second probe specifically binds to the same target molecule as the first probe or to a second target molecule that interacts with the target molecule that the first probe specifically binds to, if present in the sample, and wherein the specific binding of the second probe decreases or quenches the signal from the first probe;

partitioning the mixture into two or more partitions; and detecting the decreasing or quenching of a detectable signal generated by the first label in at least one partition; thereby detecting the target molecule or complex of target molecules in the sample.

IX. Competition Assays

In yet another aspect, methods are provided for detecting a target molecule in a sample by measuring the reduction in co-localization of signals in partitions, for example as in a competition assay. As used herein, the term "competition assay" is not limited to competitive inhibition as defined in chemistry, but rather also includes non-competitive, uncompetitive, and mixed assays. In some embodiments, the methods described herein can be used to detect a target molecule that is a component of a target molecule complex or molecular interaction, for example a component of a receptor-ligand interaction, a drug-effector interaction, an enzyme-substrate interaction, or an antibody-antigen interaction. Without being bound to a particular theory, it is believed that when a sample is highly partitioned to have a small number of probe molecules per partition, the likelihood that multiple different probes will co-localize to a particular partition by chance, rather than by specific binding to a target molecule in the partition, can be calculated. Binding of multiple different probes to a target molecule, to a complex of target molecules, or to interacting target molecules results in co-localization of the probes due to their forced physical proximity. In a partitioned competition assay sample, a first molecular component that competes with a target molecule for interaction with a second molecular component will co-localize with the second molecular component in a large number of partitions in the absence of the target molecule. The presence of target molecules in the sample decreases the rate of co-localization proportional to the amount of target molecules in the sample. Thus, for a highly partitioned sample the reduction in the number of partitions having co-localized signals in partitions can be used to measure the abundance of the target molecule in the sample.

In some embodiments, the method comprises:

incubating a sample in a mixture with at least a first probe linked to a first label and a second probe linked to a second label, wherein the first probe specifically binds to a molecular component that interacts with the target molecule and the second probe competes with the target molecule for interacting with the molecular component or binds to a second molecular component that competes with the target molecule for interacting with the first molecular component;

partitioning the mixture into two or more partitions; and detecting a reduction in the number of partitions expressing both the first label and the second label; thereby detecting the target molecule.

In some embodiments, the reduction in the number of partitions expressing both the first label and the second label is measured relative to a control sample from which the target molecule is known to be absent. In some embodiments, the number of partitions expressing both the first label and the second label is "reduced" if the number of partitions expressing both labels is decreased by at least about 1%, 2%, 3%, 4%, 5%, 10%, 15%, 20%, 25%, 30%, 35%, 40%, 45%, 50%, 60%, 70%, 80%, 90% or more as compared to the control sample (e.g., a sample from which the target molecule is known to be absent).

As one non-limiting example, in some embodiments the target molecule complex or molecular interaction is a receptor-ligand interaction. In some embodiments, the target molecule is a ligand that interacts with a receptor (the molecular component). The first probe specifically binds to the receptor, thus labeling the receptor. The second probe is a second ligand that competes with the target molecule for binding to the receptor. In some embodiments, the first and second probes are labeled with a fluorescent agent. In some embodiments, the second probe is present in excess. The target molecule (ligand) present in the sample will compete with the second probe (second ligand) for binding to the receptor and result in a decrease in the number of partitions expressing both the first probe and the second probe, proportional to the amount of target molecule present in the sample.

As another non-limiting example, in some embodiments the target molecule complex or molecular interaction is an enzyme-substrate interaction. In some embodiments, the target molecule is a substrate that specifically binds to an enzyme (the molecular component). The first probe specifically binds to the enzyme, thus labeling the enzyme. The second probe is a second substrate that competes with the target molecule for binding to the enzyme. In some embodiments, the first and second probes are labeled with a fluorescent agent. In some embodiments, the second probe is present in excess. The target molecule (substrate) present in the sample will compete with the second probe (second substrate) for binding to the enzyme and result in a decrease in the number of partitions expressing both the first probe and the second probe, proportional to the amount of target molecule in the sample.

In another embodiment, the method comprises:

incubating a sample with at least a first probe linked to a first label, wherein the first probe competes with the target molecule for interacting with a first molecular component, and wherein the first probe specifically interacts with the first molecular component in the absence of the target molecule, thereby resulting in a detectable signal in the absence of the target molecule;

partitioning the mixture into two or more partitions; and detecting a reduction in (i) the number of partitions generating a signal by co-localization of the first probe and the first molecular component; or (ii) the signal in one or more partitions;

thereby detecting the target molecule in the sample.

As one non-limiting example, in some embodiments the interaction between the molecular component and the first probe is an enzyme-substrate interaction. In some embodiments, the first probe is a substrate specifically cleaved by an enzyme (the first molecular component). In some embodiments, the target molecule is an inhibitor that competes with the first probe for binding to the enzyme.

In some embodiments, the first probe is a non-fluorescent substrate converted to a fluorescent molecular such as the conversion of 4-methylumbelliferyl phosphate (MUP) to 4-methylumbelliferone (4MU) by alkaline phosphatase as described above (e.g., in Section VI). The co-localization of the first probe and molecular component results in a detectable fluorescent signal in the absence of the target; however, in the presence of an inhibitor (e.g., levamisole), alkaline phosphatase activity is reduced, resulting in a decrease in signal intensity and/or a reduced number of partitions reaching a fluorescent threshold in a fixed time interval proportional to the amount of inhibitor (e.g., levamisole) in the sample.

Suitable probes include any of the probes described herein, e.g., in Section II above. In some embodiments, the probe is a nucleic acid (e.g., an oligonucleotide), a protein (e.g., an antibody), a non-fluorescent substrate, or an aptamer. In some embodiments, the first probe is an antibody that binds to the molecular component that interacts with the target molecule. In some embodiments, the second probe comprises a molecular component that competes with the target molecule for interacting with the molecular component.

The probes can be labeled with any detectable label as described herein, e.g., in Section II above. In some embodiments, the label is a fluorescent agent. Examples of suitable fluorescent agents that generate a fluorescent signal are described in Section II above.

X. Dilution to Improve Accuracy

The use of two or more concentrations of at least one of the components provides a mechanism to distinguish random co-localization from target dependent co-localization. When the target molecule in localized within a partition, then the probes bound to that target will co-localize due to the presence of the target. The difference between the background signal due to random co-localization and the signal when targets are present can be used to determine the concentration and/or abundance of the target molecule.

Dilution or other ways of varying concentration of one or more components of the reaction mixture is one way to improve estimates of target concentration. Dilution can be achieved by physically diluting the sample to different extents, or by virtual dilution by changing the volume assayed in each partition. In some embodiments, partitions of two or more partition sizes are generated. For example, a device that partitions the sample into two or more partition sizes, such as a droplet generator that produces at least two different sizes of monodisperse droplets, an emulsion that generates polydisperse droplets, or a plate with at least two volumes for partitioning the sample, can be used.

Dilution reduces background, but can affect dynamic range unless the number of partitions is increased as well. One solution is to increase the number of partitions, but other solutions may help as well. Use of different concentrations either globally (i.e., all components are diluted) or by diluting a subset of the reaction components is contemplated. In some embodiments, comparing co-localization with sample to a no sample control is used to determine the background vs. signal. In other embodiments, the concentrations of the other components are changed. In some cases, the binding characteristics of each probe will be different. In some embodiments, running the same sample at different concentrations of sample, or different concentrations of one or more probes, generates different effects for specific vs. non-specific binding. In some embodiments, increasing (for example doubling) one probe concentration has a very specific effect on the random distribution causing that number to nearly double (with the precise increase predictable by poisson statistics for a given number of partitions), but has a limited effect on the specific binding as long as the probe concentration is saturating for that target. Likewise, in some embodiments, decreasing probe concentration has one effect on the non-specific co-localization and a different effect of the specific co-localization of probes. In some embodiments, the sample mixture is subdivided with some subdivisions being subsequently diluted further, thereby providing a mechanism to distinguish specific from random co-localization. If a particular subdivision is diluted into a larger number of subdivisions, the number of co-localizations due to binding should stay the same but the number of random co-localizations should decrease by an amount predictable by the dilution factor, number of partitions, and the number of probes. The frequency of co-localization due to binding should decrease as well, although the number of targets will not change. Thus even if the "dilution" is virtual (for example smaller droplets) the co-localization due to binding will only decrease in frequency in a manner predictable by the dilution factor and not decrease in absolute amount, but the random co-localization will decrease by a much higher factor and thus serves as a mechanism to distinguish target from random co-localization. This approach can similarly be used to distinguish random from specific binding for single probe assays.

At a low concentration of probe(s) all of the target molecules are not bound to both probes. At this point, increasing the probe concentration will increase the number of dual positives due to the presence of the target. Once all the targets have both probes bound, adding more probe will not change the number of dual positives due to the presence of target. However, the number of observed dual positives is made up of both the target molecules and dual positives due to random chance. The number of dual positives due to random chance can be changed by explicitly altering the number of dual positives. In situations where the probe concentration is sufficient to saturate the target, increasing the amount of unbound probe such that the amount of the random co-localization changes in a predictable manner (e.g., doubles) can assist in calculation of random co-localization. For example, the increase in co-localization resulting from increase in probe concentration is proportional to the original contribution due to random co-localization. The increase in observed dual positives with a known additional input allows calculation of the previous random co-localization and thus also the target dependent co-localization. Likewise, by decreasing the concentration we can similarly determine the target amount by comparison. Optionally, it is possible to plot the decrease in dual positives with concentration of probe and/or target. In some embodiments, where the rate of decrease deviates in such a plot is where the target is no longer fully bound. Alternatively, in some embodiments, if the concentration of target is known (for example by the measurements at higher probe concentrations) then the point of deviation in co-localization rate and/or subsequent rate of decrease provides information about the interaction of probe and target.

XI. Partition Libraries

In another aspect, the present invention relates to partition libraries comprising a plurality of partitions for carrying out the methods as described herein. In some embodiments, the partition library comprises two or more partitions, wherein at least some partitions of the library (e.g., at least 5%, 10%, 15%, 20%, 25%, 30%, 35%, 40%, 45%, 50%, 55%, 60%, 65%, 70%, 75%, 80%, 85%, 90%, or 95% of the partitions in the library) comprise a first probe comprising a first label and a second probe comprising a second label. In some embodiments, the partition library comprises at least 500, 1000, 2000, 3000, 4000, 5000, 6000, 7000, 8000, 10,000, 15,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 10,000,000, 20,000,000, 30,000,000, 40,000,000, 50,000,000, 60,000,000, 70,000,000, 80,000,000, 90,000,000, 100,000,000, 150,000,000, or 200,000,000 partitions.

The probes and probe labels for the partitions of the partition library can be any probe or probe label described herein. In some embodiments, the first probe and/or the second probe comprises a binding agent selected from the group consisting of antibodies, aptamers, and non-antibody protein scaffold. In some embodiments, the first and second labels are nucleic acids, fluorescent moieties, affinity tags, or click chemistry moieties, and wherein the first label is different from the second label. In some embodiments, the first label and the second label combine to produce a signal that is not generated in the absence of the first label, the second label, or both. In some embodiments, the first label generates a first signal and the second label generates a second signal and the first signal and the second signal are distinguishable.

In some embodiments, the partition library comprises a sufficient number of partitions such that co-localization of the probes due to binding of a target molecule can be distinguished from random co-localization. In some embodiments, at least 1 partition of the partition library has 0 copies of the target molecule. In some embodiments, at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions of the partition library, or more, have 0 copies of the target molecule. In some embodiments, at least 1 partition of the partition library has 0 copies of the target molecule and at least 1 partition of the partition library has 1 or more copies (e.g., 1, 2, 3, 4, 5, 6, 7, 8, 9, 10 or more copies) of the target molecule. In some embodiments, at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions of the partition library, or more, have 0 copies of the target molecule and at least about 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions of the partition library, or more, have 1 or more copies (e.g., 1, 2, 3, 4, 5, 6, 7, 8, 9, 10 or more copies) of the target molecule. In some embodiments, the partition library comprises a sufficient number of partitions such that the two or more probes do not co-localize in at least 1 partition. In some embodiments, the partition library comprises a sufficient number of partitions such that the probes do not co-localize in at least 1, 2, 3, 4, 5, 6, 7, 8, 9, 10, 15, 20, 25, 30, 40, 50, 60, 70, 80, 90, 100, 150, 200, 250, 300, 400, 500, 600, 700, 800, 900, or 1000 partitions or more.

In some embodiments, at least some partitions of the partition library comprise one or more target molecules. In some embodiments, at least some partitions comprise two, three, four, five, or more different target molecules. In some embodiments, on average no more than 5 copies (e.g., no more than 5 copies, no more than 4 copies, no more than 3 copies, no more than 2 copies, or no more than 1 copy) of the one or more target molecules are present in each partition.

In some embodiments, the partition library comprises a plurality of partitions that are solid partitions (e.g., wells or tubes). In some embodiments, the partitions are microchannels. In some embodiments, the partition library comprises a plurality of partitions that are fluid partitions (e.g., aqueous droplets within an oil phase). In some embodiments, the partitions are droplets. In some embodiments, the partitions are microcapsules. Examples of suitable partitions and methods of generating partitions are described above.

In some embodiments, the partition library comprises partitions that are substantially uniform in shape and/or size. For example, in some embodiments, the partitions (e.g., droplets) are substantially uniform in average diameter. In some embodiments, the partitions (e.g., droplets) have an average diameter of about 0.001, 0.005, 0.01, 0.05, 0.1, 0.5, 1, 5, 10, 20, 30, 40, 50, 60, 70, 80, 90, 100, 150, 200, 300, 400, 500, 600, 700, 800, 900, or 1000 microns. In some embodiments, the partitions (e.g., droplets) have an average diameter of less than about 1000, 900, 800, 700, 600, 500, 400, 300, 200, 100, 50, or 25 microns. In some embodiments, the partition library comprises partitions (e.g., droplets) that are non-uniform in shape and/or size.

In some embodiments, the partitions (e.g., droplets) are substantially uniform in volume. For example, in some embodiments, the partitions (e.g., droplets) have an average volume of about 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, or 50 nL.

In some embodiments, the partitions (e.g., droplets) are stable and are capable of long-term storage. In some embodiments, the partitions can be stored at about −70°, −20°, 0°, 3°, 4°, 5°, 6°, 7°, 8°, 9°, 10°, 15°, 20°, 25°, 30°, 35°, or 40° C. for an extended period of time (e.g., for at least 30 days, at least 60 days, at least 90 days, or longer).

EXAMPLES

The following examples are offered to illustrate, but not to limit the claimed invention.

Example 1: Estimation of Concentration of a Target Molecule

This example provides a statistical framework for estimating the concentration of a target molecule in a sample by measuring the concentration of molecules that are positive for two different probes (FAM and VIC) in each partition (e.g., droplet).

Figure 5:
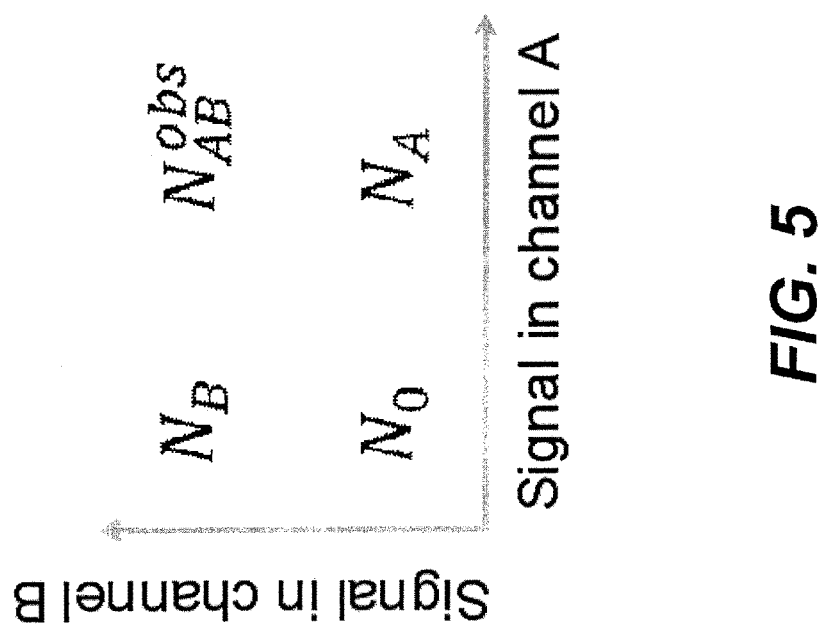
FIG. 5. Estimation of concentration of linked species in a sample. In a sample in which two probes are used, probe A (e.g., with the detectable label FAM) and probe B (e.g., with the detectable label VIC), both of which are capable of specifically binding the same target molecule, four possible events can be observed: $N_0$ (negative for both probes), $N_A$ (positive for probe A but negative for probe B), $N_B$ (positive for probe B but negative for probe A), and $N_{AB}$ (positive for both probes). $N_0$, $N_A$, $N_B$, and $N_{AB}$ are measured unambiguously. Some of the observed double-positive events (e.g., droplets) will be due to chance localization of single species in droplets, while some will be due to the actual presence of linked molecules. The concentration of linked molecules can be estimated as described in Example 1.

For this example, two probes are used: probe A (e.g., with detectable label FAM) and probe B (e.g., with detectable label VIC), both of which are capable of specifically binding the same target molecule. Four possible events can be observed: $N_0$ (negative for both probes), $N_A$ (positive for probe A but negative for probe B), $N_B$ (positive for probe B but negative for probe A), and $N_{AB}$ (positive for both probes) (FIG. 5). For each droplet, the event is measured unambiguously. Some of the observed double positive droplets ($N_{AB}$) will be due to chance localization of single species in droplets ($N_{chance\ AB}$), while some of the $N_{AB}$ will be due to the actual presence of co-localized probes on a target molecule ($N_{co\text{-}local\ AB}$).

When no co-localized probes on a target molecule are present, there are no systematic biases in the system, and A and B are uncorrelated. In such a scenario, $N_{chance\ AB}$ can be estimated as:

$$N_{chance\ AB} = (N_A N_B)/N_0$$

When co-localized probes on a target molecule are present, the chance counts ($N_{chance\ AB}$) must be subtracted from the observed counts ($N_{obs\ AB}$):

$$N_{co\text{-}local\ AB} = N_{obs\ AB} - N_{chance\ AB} = N_{obs\ AB}(N_A N_B)/N_0$$

We can then use the following formula to compute the concentration of co-localized probes on a target molecule:

$$\lambda_{co\text{-}local} = \ln(N_{tot}) - \ln(N_0 + N_A + N_B + ((N_A N_B)/N_0)$$

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting a target molecule in a sample, the method comprising:
   incubating said sample in a mixture with at least a first probe linked to a first label and a second probe linked to a second label, wherein the first and second probes specifically bind the same target molecule, if present;
   partitioning the mixture into two or more partitions, wherein on average the partitions have fewer than two probes; and
   detecting the presence of the first label and the second label in at least one same partition, thereby detecting the target molecule in the sample.

2. The method of claim 1, wherein the partitioning comprises generating a sufficient number of partitions such that co-localization of the probes due to binding of a target molecule can be distinguished from random co-localization.

3. The method of claim 1, wherein the first and second labels comprise nucleic acids, fluorescent moieties, affinity tags, or click chemistry moieties, and wherein the first label is different from the second label.

4. The method of claim 1, wherein the first label generates a first signal and the second label generates a second signal and the first signal and the second signal are distinguishable.

5. The method of claim 4, wherein the first label is a first enzyme and the second label is a second enzyme, and the detecting comprises detecting products generated by the first and second enzymes.

6. The method of claim 1, wherein the first label and the second label combine to produce a signal that is not generated in the absence of the first label, the second label, or both.

7. The method of claim 6, wherein the first label is a first enzyme and the second label is a second enzyme and the activities of the first and second enzymes combine to generate a detectable signal indicative of the presence of the first and second labels.

8. The method of claim 1, wherein the signal from the first label and the signal from the second label are amplified following the partitioning.

9. The method of claim 1, further comprising determining the number of partitions comprising the first label and the second label.

10. The method of claim 1, wherein the partitions are droplets or microchannels.

11. The method of claim 1, wherein the target molecule is a protein or a nucleic acid.

12. The method of claim 1, wherein the first probe and/or the second probe comprises (i) a binding agent independently selected from the group consisting of antibodies, aptamers, and non-antibody protein scaffolds, or (ii) a target-specific binding agent independently selected from the group consisting of a nucleic acid and a zinc finger protein.

13. A method of detecting a target molecule in a sample, wherein the target molecule is linked to, or is capable of generating, a detectable molecule, the method comprising:
    incubating the sample in a mixture with a first probe linked to a first label, wherein the first probe specifically binds the target molecule, if present;
    partitioning the mixture into two or more partitions, wherein on average the partitions have fewer than one probe; and
    detecting the presence of the first label and the detectable molecule in at least one same partition, thereby detecting the target molecule in the sample.

14. The method of claim 13, wherein the target molecule is an enzyme capable of converting a substrate in the mixture into the detectable molecule or into an intermediate molecule that is further converted into the detectable molecule by the first label.

* * * * *